United States Patent [19]

Jang et al.

[11] Patent Number: 5,681,580
[45] Date of Patent: Oct. 28, 1997

[54] PATCH-TYPE DEVICE FOR IONTOPHORETIC TRANSDERMAL DELIVERY OF INSULIN

[75] Inventors: Kwang Kyun Jang, Kyungki-Do; Young Sig Oh, Seoul, both of Rep. of Korea

[73] Assignee: Samsung Electro-Mechanics Co., Ltd., Kyungki-do, Rep. of Korea

[21] Appl. No.: 448,235

[22] Filed: May 23, 1995

[30] Foreign Application Priority Data

May 23, 1994 [KR] Rep. of Korea ............. 94-11251

[51] Int. Cl.⁶ ................... A61N 1/30; A61M 37/00
[52] U.S. Cl. ............... 424/449; 602/50; 604/304; 607/152; D24/187; D24/189
[58] Field of Search ............... 424/449; 602/50; 604/20, 289, 290, 304; 607/152; 824/189

[56] References Cited

U.S. PATENT DOCUMENTS

| | | | |
|---|---|---|---|
| 4,940,456 | 7/1990 | Sibalis et al. | 424/449 |
| 5,135,480 | 8/1992 | Bannon et al. | 604/20 |
| 5,288,289 | 2/1994 | Haak et al. | 604/20 |
| 5,362,308 | 11/1994 | Chien et al. | 604/20 |
| 5,533,995 | 7/1996 | Corish et al. | 424/449 |

FOREIGN PATENT DOCUMENTS 92-2264  3/1992  Rep. of Korea.

*Primary Examiner*—Edward J. Webman

[57] ABSTRACT

The present invention is a patch-type device for iontophoretic transdermal medication of insulin of one-piece form having a container for holding gel-like insulin and a power supply for furnishing insulin with electricity. A patch plate, formed with an embossed portion, electrically contacts an electrode pattern formed in a printed circuit board carried by the device, thereby improving transdermal treatment of insulin.

14 Claims, 4 Drawing Sheets

PATCH-TYPE DEVICE FOR IONTOPHORETIC TRANSDERMAL DELIVERY OF INSULIN

FIELD OF THE INVENTION

The present invention relates to a patch-type device for use in transdermal delivery of insulin, and more particularly, to a patch-type device which can provide a releasable attachment between a container of the insulin and a power supply for supplying electric current to the insulin.

DESCRIPTION OF THE PRIOR ART

As is generally known in the art, insulin works well in medical treatment of diabetics and consists of macromolecules whose molecular weight is more than 600. Due to their size, insulin molecules have difficulty penetrating the skin of diabetics even if the nature of the skin is changed by proper chemical treatment with a solvent. More specially, insulin, as a polypeptide consisting of amino acids, is a highly hydrophilic drug and has little affinity with the epidermis of the skin which is intrinsically hydrophobic. Thus, the insulin cannot penetrate the epidermis and enter the bodily skin. Accordingly, the inability of insulin to penetrate the skin tends to make its trandermal administration less appropriate. Recently, several patch-type devices for transdermal administration of insulin have been developed, which enable delivery of insulin into blood through the skin.

Anatomically, the skin of human body can be subdivided into an epidermis, a dermis and an endodermis, of which the epidermis plays a key role in blocking drug delivery via the skin. The epidermis is 0.1 mm or more in its thickness and consists of about 20% lipid and about 40% protein, among other things. Each segment of protein is surrounded by lipid, thus rendering the epidermis hydrophobid. Also, as compared with the water content of more than 70% of the dermis and the endodermis respectively, the epidermis contains no more than 40% water. Accordingly, the epidermis has a tendency to exhibit an increased electrical resistance and serves to protect the dermis from thermal attack or external stimulus.

Korean Patent Publication No. 92-2264 discloses a patch-type device for transdermally applying insulin to the body of diabetics. The insulin delivery device comprises an insulin solvent-filled reservoir constituting a framework of the device, a water-swellable, and insulin-carrying polymeric supporting layer on which insulin is dispersed in a power form, a needle support adapted to expand as the insulin solvent is discharged from the reservoir, a multiplicity of skin perforation needles extending vertically from the needle support so as to come into contact with the bodily skin and an electrode attached to the ceiling of the reservoir for supplying the reservoir and the bodily skin with electricity.

In accordance with the above-referenced insulin delivery device, the skin perforation needles act to create passageways on the epidermis of the skin when they are pressed against the skin. The passageways will be then closed off for a while due mainly to the swelling of the perforated skin. Applying direct current or alternating current to the electrode housed within the ceiling of the reservoir will cause the ionized insulin and solvent to move toward the opposite electrode, in which the hydrophilic proteins and polypeptides of the skin would be arranged in parallel with repect to the anode, thereby resulting in shrinkage of the skin and enlargement of the passageways. This eventually allows insulin to penetrate into the hypodermis.

However, the above-referenced device is economically expensive for consumers in that it is presented as an integrated form which includes both the reservoir and the needles, and is provided as a disposable device which is to be discarded after use.

To overcome the above-mentioned drawbacks, a skin perforation needle pretreatment device has been proposed in which a patch plate and a needle driving apparatus are separately provided. However, the pretreatment device must first function by creating thousands of fine cuts on a specific treatment area before application of insulin to the skin. Then, the insulin is separately administered to the skin after the pretreatment. This is inconvenient to users.

SUMMARY OF THE INVENTION

The present invention is directed to overcoming the problems inherent in the prior art.

Accordingly, it is an object of the invention to provide a patch-type device which can be used for transdermal administration of insulin and be easily fabricated in slim-type structure without molding a one-piece form of a patch plate and a needle driving apparatus.

Another object of the invention is to provide a patch-type device which can provide a releasable attachment between a container filled with insulin and a power supply for supplying electric current to the insulin, and an electrical connection between a patch plate and a printed circuit board.

In one aspect of the present invention, there is provided a patch-type device for transdermal medication of insulin which comprises:

- a patch main body having a first recess portion for receiving gel-like insulin in at least one side thereof, and a receiver which includes a plurality of fixed recesses and a second recess positioned in an opposing surface of the first recess;
- a grounded board attached to the second recess of the patch main body; and
- a conductive patch plate being fixedly connected with the lower surface of the main body to create a bottom of the first recess and having a plurality of embossing portions which are horizontal and protrude downward or upward from an angled portion of the bottom.

In another aspect of the present invention, there is provided a patch-type device which comprises:

- a patch main body having a first recess portion for receiving gel-like insulin in at least one side thereof, and a receiver which consists of a plurality of fixed recesses and a second recess positioned in an opposing surface of the first recess;
- a grounded board attached to the second recess of the patch main body;
- a conductive patch plate being fixedly connected with the lower surface of the said body to create a bottom of the first recess and having a plurality of embossing portions which are horizontal and protrude downward or upward from an angled portion of the bottom; and
- a power supply comprising a printed circuit board and a cap for the protection of the said printed board, the circuit board being entirely fitted into the conductive patch plate and the receiver of the patch main body, and having various kinds of circuit elements and an electrode pattern, the circuit elements being used for supplying the patch plate itself with electric power and the electrode pattern being made of copper sheet, placed on the opposing surface of the elements, and capable of providing an electrical connection with the patch plate, and the protective cap serving to wrap the printed circuit board externally.

BRIEF DESCRIPTION OF THE DRAWINGS

The above and other objects, features and advantages of the invention will become apparent from a review of the following description of the preferred embodiments taken in conjunction with the accompanying drawings, in which.

DETAILED DESCRIPTION OF THE PREFERRED EMBODIMENTS

Figure 1:
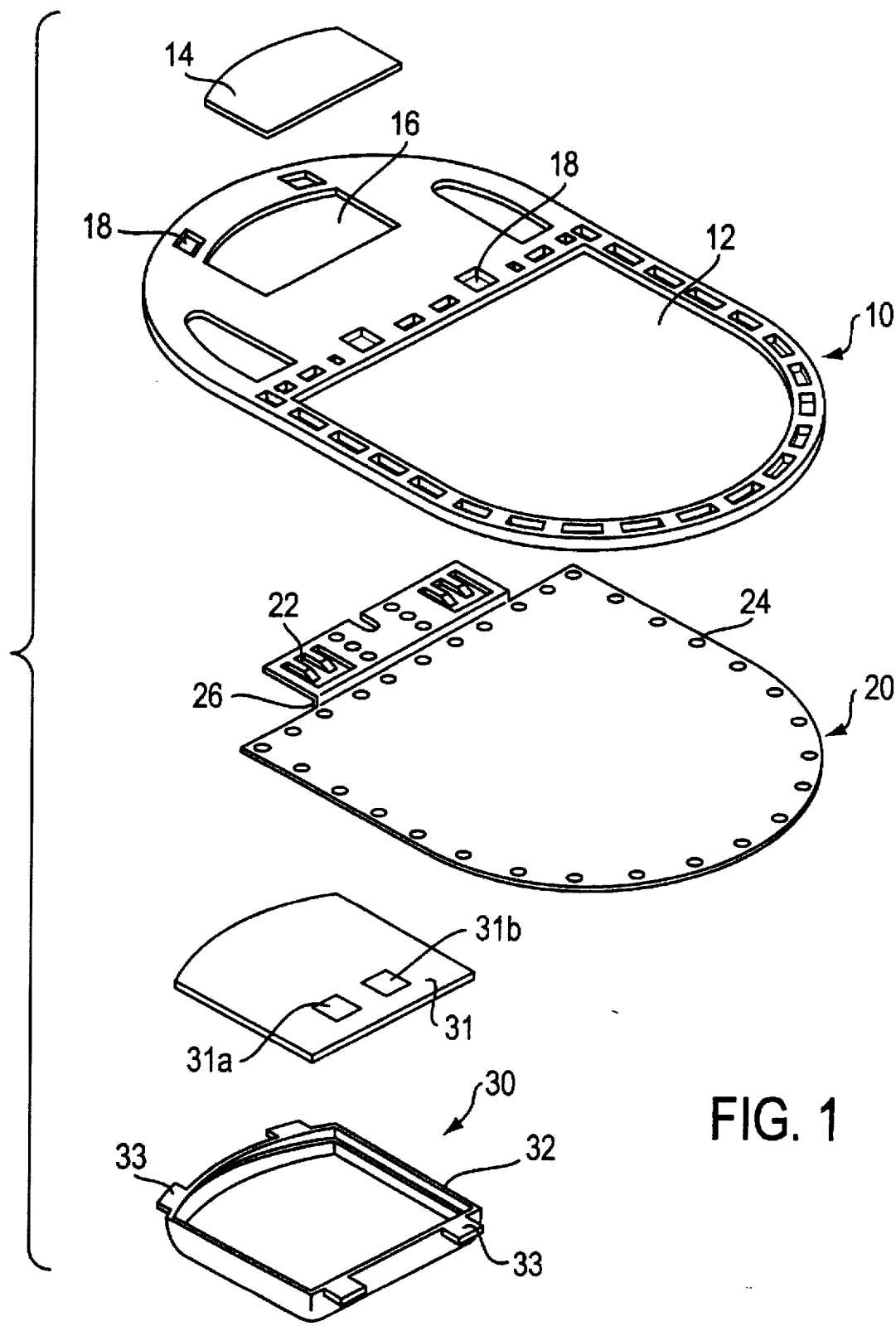
FIG. 1 is a exploded perspective view of the insulin patch device in accordance with the first embodiment of the invention.

Referring to FIG. 1 a main body 10 of the patch device comprises a first recess portion 12 to receive gel-like insulin (not shown), a second recess portion 16 to receive a grounded board 14 hereinafter described, and a plurality of fixed recesses 18 to fix the power supply. Below, the second recess 16 and the fixed recess 18 are named as receiver portions.

Figure 3:
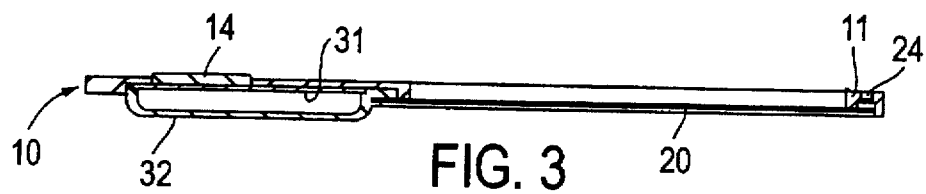
FIG. 3 is a partially enlarged sectional view taken approximately along line III—III of FIG. 2.
Figure 4:
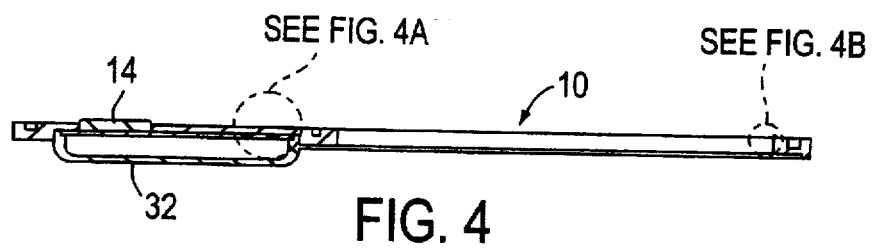
FIG. 4 is a partially enlarged sectional view taken approximately along line IV—IV of FIG. 2.
Figure 4A:
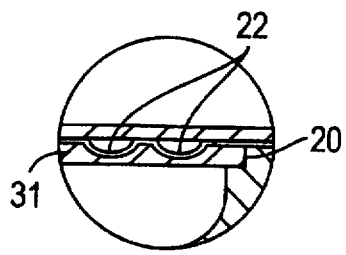
Figure 4B:
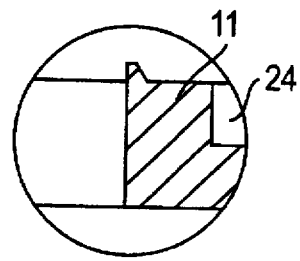

A patch plate 20 made of good electric conductive materials is formed in the interior of body 10 as an integrated unit. The front portion of the patch board 20 is curved slightly higher than the main body, and has an embossed portion 22 to enable easy electrical connection with the printed circuit board 14. The embossed portion 22 has a plurality of downward projecting elastic contacts, as clearly shown in FIG. 4. Also, a plurality of holes 24 are formed in the peripheral portion of patch plate 20 for lugged connection with the main body 10, i.e., the main body may be formed of soft materials 11 (FIG. 3) (e.g., resin or rubber) which are respectively inserted into the holes 24 to allow the plate 20 to be joined to the main body when the engagement of the main body with the patch plate is made as depicted in FIGS. 3 and 4.

Figure 2:
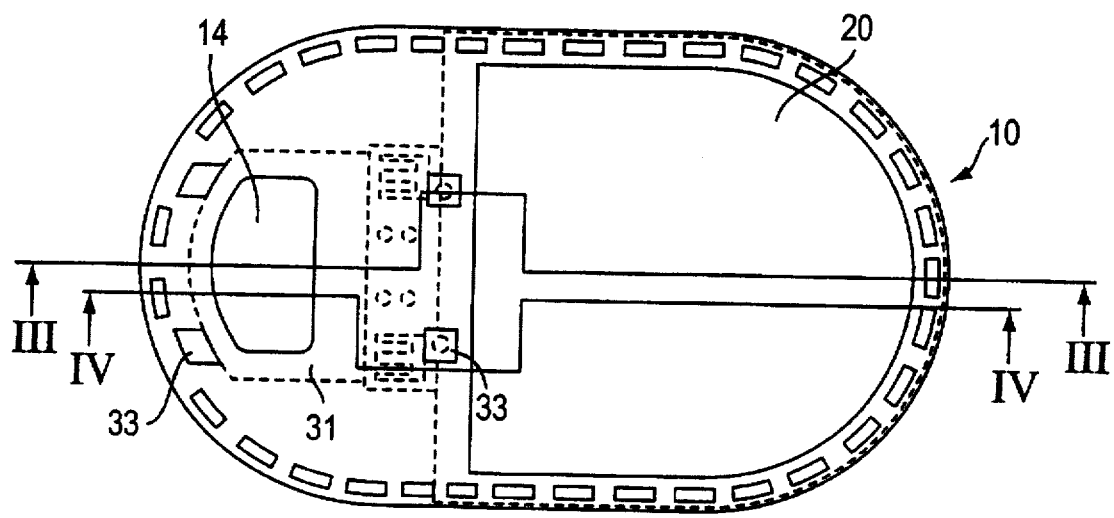
FIG. 2 is a partially enlarged view illustrating the insulin patch device shown in FIG. 1.

FIG. 2 shows that the front portion of the patch plate 20 also comprises an angled portion which facilitates contact with tabs of the power supply cap as described below.

The power supply 30 encompasses a printed circuit board 31 comprised of appropriate circuit elements to provide an electric current (direct current or alternating current) to the patch plate 20 on which insulin will be placed, and a power supply protective cap 32 for protecting the printed circuit board 31.

As in FIG. 1, a copper sheet 31a, 31b capable of contacting with embossed portion 22 of the patch plate is formed on the printed circuit board in order to provide the patch plate with the electric current output from the circuit elements downward of the printed board through the embossing portion (contacts).

The power supply protective cap, which encompasses the printed circuit board 31 in its interior, has four tabs which are inserted into four holes 18 of the main body 10, making it possible to connect the electric power supply to the main body.

The patch-type device used for transdermal administration of insulin according to the invention set forth above can be fabricated by attaching patch plate 20 to the lower surface of the main body; inserting printed circuit board 31 into protective cap 32 and fixing it; connecting and engaging grounded board 14 to the upper portion of the printed circuit board 31; inserting tabs 33 which are formed in the protective cap 32 of the power supply 30 into a fixed recesses 18 of the main body, thereby attaching the main body to the supply; disposing gel-like insulin solvent (not shown) on first recess portion 12; carrying out the pretreatment to the desired skin region by the pretreatment device (not shown) under the insulin solvent-disposed stated; and applying means such as a bandage.

When the insulin patch is laid on the skin region, the grounded board forms a closed circuit to allow the insulin to be ionized and transdermally delivered through the fine skin cuts.

As magnified and shown in FIG. 4, it can be seen that the front portion of the patch plate 20 comprises embossed portion 22 protruding downward to make it possible to generate a concrete and effective electrical connection with a copper sheet of the printed circuit board 31 so that insulin can easily penetrate the skin region.

Figure 5:
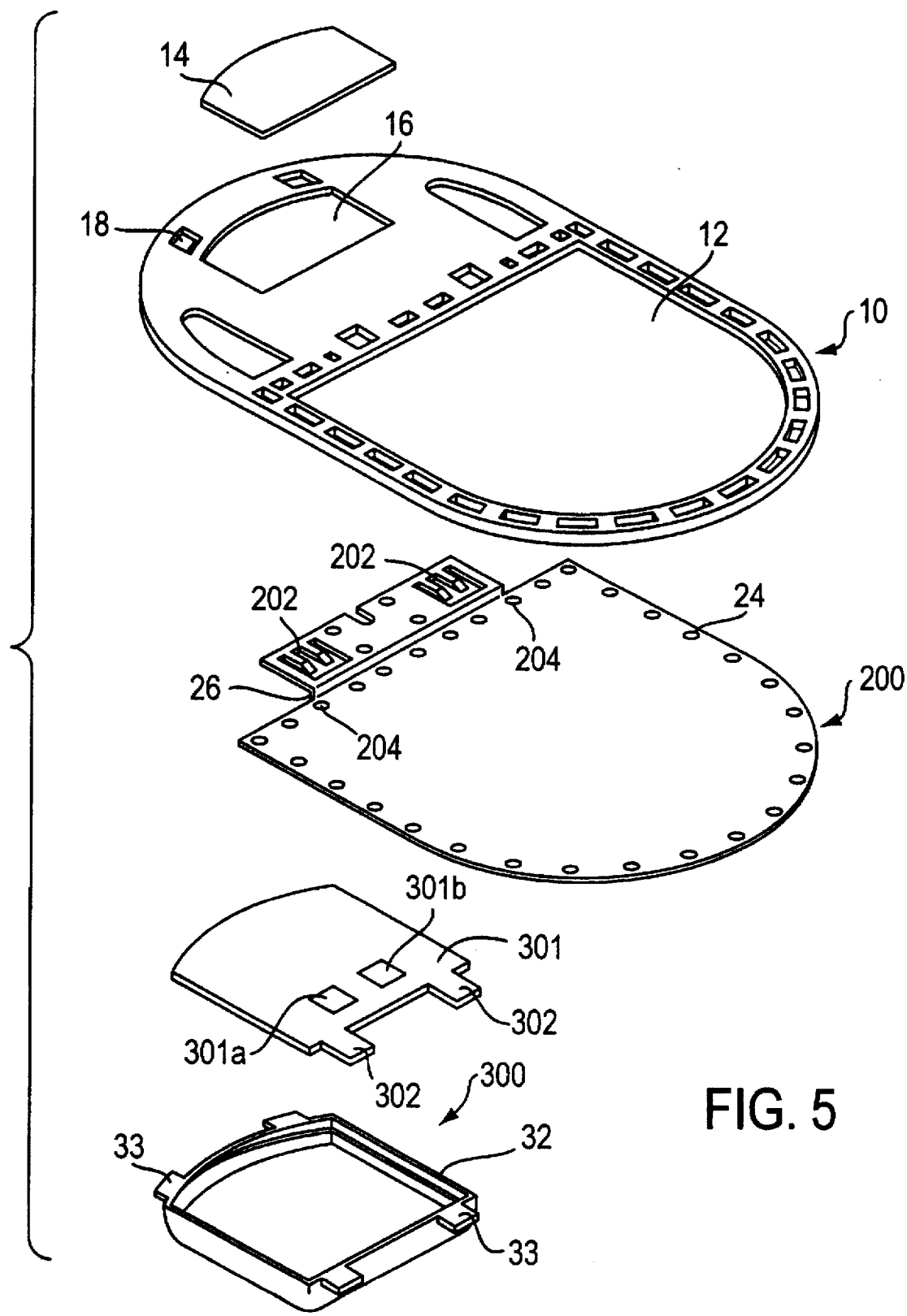
FIG. 5 is a partially enlarged sectional view in accordance with the second embodiment of the invention.
Figure 6:
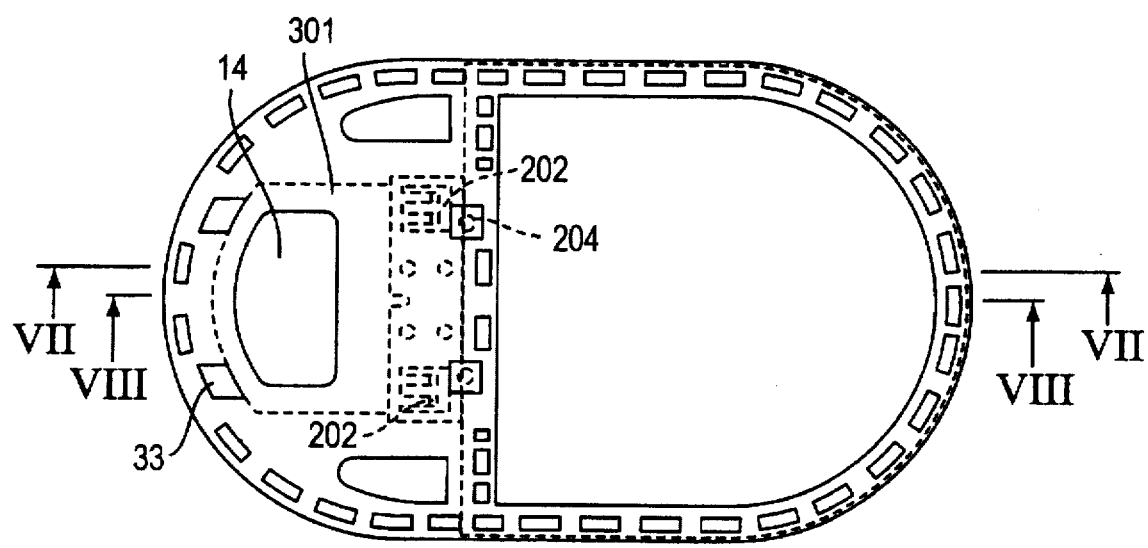
FIG. 6 is an assembled planar view of the insulin patch device shown in FIG. 5.

FIG. 5, is an exploded perspective view according to the second embodiment of the invention, wherein the same or the like reference numerals designates the same or the like parts or components, and therefore, repetitive description is avoided.

The patch main body 10 is made of a flexible material such as resin, rubber and the like. As depicted in FIG. 5, but unlike FIG. 1 of the patch plate, the plate has two embossed portions 202 in the front portions of the plate, the embossed portion being downwardly projected with respect to the front portion. The circumference of the patch plate has a plurality of holes which are completely fitted into the main body. The plate has also other embossed portions 204 which are upwardly projected from the plate and which are positioned near the tabs 33 of the protective cap 32 of the power supply. Accordingly, the embossed portions 202, 204 consist of a number of contacts having elasticity to render engagement with the power supply readily. In addition, contacts of the copper sheets are formed in two leg portions 302 of the printed circuit board 301, these leg portions making it possible to bring into contact with the embossed portion 204 of the patch plate 200, thereby guaranteeing the definite electric connection with the conductive patch plate 200. Because of the copper sheets 301a, 301b and the leg portion 302 formed in the printed circuit board 301, the printed board and the patch plate can have a concrete electrical connection.

Figure 7:
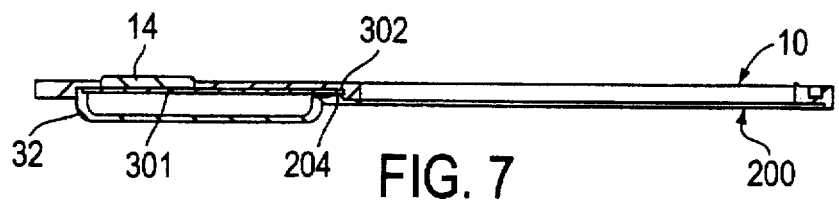
FIG. 7 is a partially enlarged sectional view taken approximately along line VII—VII of FIG. 6.
Figure 8:
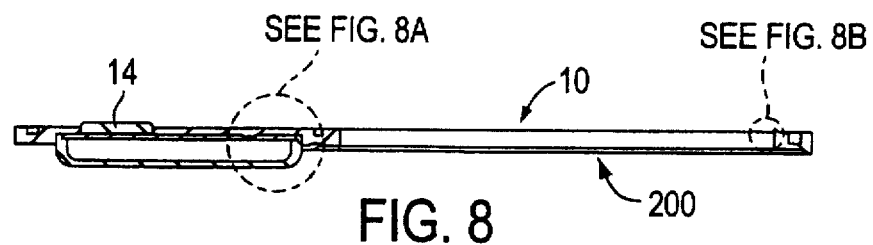
FIG. 8 is a partially enlarged sectional view taken approximately along line VIII—VIII of FIG. 6.
Figure 8A:
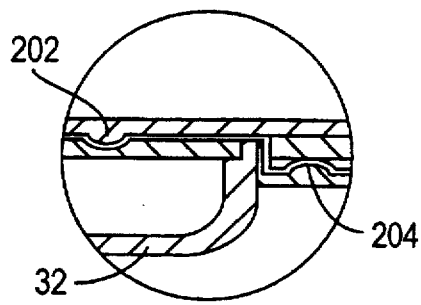
Figure 8B:
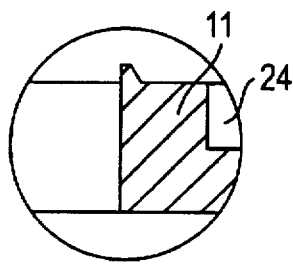

Turning to FIGS. 7 and 8, it can be seen that the upper portion and the lower portion of the printed circuit board 301 are conjoined with the patch plate 200 and thus a complete electrical connection is obtained since even if one portion is separated, another portion's contact can be securely maintained.

As set forth in detail herein above, the inventive insulin patch device is able to be fabricated as a slim type so that it is very convenient to use and reveals an excellent effect which is a result of a concrete electrical connection between the printed circuit board and the patch plate through the embossed portion.

The invention has now been described with reference to the embodiments thereof. It will be appreciated that many modifications and changes can be made in the structure of the patch-type device above mentioned without departing from the spirit of the invention. Thus the scope of the claims in this application should not be limited by the device described herein, but only by the structures described by the language of the claims and their equivalents.

What is claimed is:

1. A patch device for transdermal administration of insulin, comprising:

a patch main body having a first recess portion adapted for receiving a gel-like insulin, and a receiver portion which includes a plurality of fixed recesses and a second recess;

a grounded board attached to the second recess of the patch main body; and a conductive patch plate being fixedly connected with a lower surface of said main body to form a bottom of the first recess and having a plurality of embossing portions which protrude from an angled portion of the patch plate.

2. The patch-type device as recited in claim 1, wherein said patch main body is flexible.

3. The patch-type device as recited in claim 1, wherein said patch main body is made of resin.

4. The patch device as recited in claim 1 wherein said patch main body is made of rubber.

5. The patch type device as recited in claim 1, wherein said embossing portion form electrical contacts.

6. The patch device as recited in claim 5 wherein said contacts are elastically deformable.

7. The patch device as recited in claim 1 wherein a plurality of holes are formed in the circumference of the patch plate for engagement with the patch main body.

8. A patch device adapted for transdermal administration of insulin, comprising:

a patch main body having a first recess portion adapted for receiving a gel-like insulin, and a receiver portion which includes a plurality of fixed recesses and a second recess;

a grounded board attached to the second recess of the patch main body;

a conductive patch plate being fixedly connected with a lower surface of said main body to form a bottom of the first recess and having a plurality of embossing portions which protrude from an angled portion of the patch plate; and a power supply comprising a printed circuit board and a cap for the protection of said printed board, said circuit board being entirely fitted adjacent the conductive patch plate and the receiver portion of the patch main body and having circuit elements and an electrode pattern, the circuit elements being used for supplying the patch plate with electric power and the electrode pattern being made of conductive metal placed on an opposing surface of the circuit element and capable of providing electric connection with the patch plate.

9. The patch device as recited in claim 8, wherein the said conductive patch plate comprises a plurality of electrical contacts to be contacted with the electrode pattern of the printed circuit board.

10. The patch device as recited in claim 8 wherein the contacts are elastically deformable.

11. The patch device as recited in claim 8 wherein the printed circuit further comprises at least two leg portions for ensuring electrical connection with the conductive patch plate.

12. The patch device as recited in claim 8, wherein the patch main body is flexible.

13. The patch-body as recited inh claim 8, wherein the patch main body is made of resin.

14. The patch-body as recited in claim 8, wherein the patch main body is made of rubber.

* * * * *